United States Patent
Holzner et al.

(10) Patent No.: US 9,290,632 B2
(45) Date of Patent: Mar. 22, 2016

(54) ELASTOMER PRODUCT WITH COVALENTLY BONDED PARTICLES

(71) Applicant: SEMPERIT AKTIENGESELLSCHAFT HOLDING, Vienna (AT)

(72) Inventors: Armin Holzner, Ternitz (AT); Wolfgang Kern, Seiersberg (AT); Dietmar Lenko, Graz (AT); Jakob Cornelius Manhart, Leoben (AT); Raimund Schaller, Neunkirchen (AT); Sandra Schloegl, Stallhofen (AT)

(73) Assignee: SEMPERIT AKTIENGESELLSCHAFT HOLDING, Vienna (AT)

( * ) Notice: Subject to any disclaimer, the term of this patent is extended or adjusted under 35 U.S.C. 154(b) by 227 days.

(21) Appl. No.: 14/047,588

(22) Filed: Oct. 7, 2013

(65) Prior Publication Data
US 2014/0096308 A1  Apr. 10, 2014

(30) Foreign Application Priority Data

Oct. 9, 2012 (AT) .................................. A 1087/2012

(51) Int. Cl.
| | |
|---|---|
| C08J 7/14 | (2006.01) |
| B32B 5/30 | (2006.01) |
| B32B 19/04 | (2006.01) |
| B32B 25/02 | (2006.01) |
| C08C 19/06 | (2006.01) |
| C08K 7/18 | (2006.01) |
| C08K 7/22 | (2006.01) |
| C08K 9/04 | (2006.01) |

(Continued)

(52) U.S. Cl.
CPC ... *C08J 7/14* (2013.01); *B32B 5/30* (2013.01); *B32B 7/10* (2013.01); *B32B 19/04* (2013.01); *B32B 25/02* (2013.01); *B32B 27/08* (2013.01); *B32B 27/14* (2013.01); *B32B 27/283* (2013.01); *B32B 27/40* (2013.01); *C08C 19/06* (2013.01); *C08K 7/18* (2013.01); *C08K 7/22* (2013.01); *C08K 9/04* (2013.01); *C08K 9/08* (2013.01); *A61B 19/04* (2013.01); *B32B 2264/0214* (2013.01)

(58) Field of Classification Search
None
See application file for complete search history.

(56) References Cited

U.S. PATENT DOCUMENTS

| | | | |
|---|---|---|---|
| 5,310,819 A | * | 5/1994 | Roland ...................... C08J 7/12 524/245 |
| 5,804,318 A | | 9/1998 | Pinchuk et al. |

(Continued)

FOREIGN PATENT DOCUMENTS

| | | |
|---|---|---|
| AT | 502764 A1 | 5/2007 |
| AT | 508099 A1 | 10/2010 |

(Continued)

OTHER PUBLICATIONS

Amornchaiyapitak, European Polymer Journal, vol. 44 (2008) p. 1782-1788.*

(Continued)

*Primary Examiner* — Robert C Boyle
(74) *Attorney, Agent, or Firm* — Greenblum & Bernstein, P.L.C.

(57) ABSTRACT

The invention relates to a method of bonding particles to the surface of an elastomer, in particular a glove, the surface of the elastomer being at least partially epoxidized, and the particles are covalently bonded to the epoxide groups after epoxidation of the elastomer surface.

10 Claims, 1 Drawing Sheet

(51) Int. Cl.

| | |
|---|---|
| *C08K 9/08* | (2006.01) |
| *B32B 7/10* | (2006.01) |
| *B32B 27/08* | (2006.01) |
| *B32B 27/14* | (2006.01) |
| *B32B 27/28* | (2006.01) |
| *B32B 27/40* | (2006.01) |
| *A61B 19/04* | (2006.01) |

(56) References Cited

U.S. PATENT DOCUMENTS

| | | |
|---|---|---|
| 6,797,783 B1 | 9/2004 | Tanaka et al. |
| 6,903,165 B2 | 6/2005 | Yabui et al. |
| 7,441,746 B2 | 10/2008 | Sugiyama |
| 7,442,746 B2 * | 10/2008 | Parker .................... C08C 19/06 524/815 |
| 2003/0190490 A1 | 10/2003 | Kaya et al. |
| 2004/0258884 A1 * | 12/2004 | Janssen .......................... 428/143 |
| 2006/0074185 A1 * | 4/2006 | Ganapathiappan et al. .. 524/800 |
| 2007/0049659 A1 | 3/2007 | Quay |
| 2009/0136746 A1 * | 5/2009 | Murai et al. ................... 428/339 |

FOREIGN PATENT DOCUMENTS

| | | |
|---|---|---|
| DE | 10260219 B | 10/2003 |
| GB | 1396090 A | 5/1975 |

OTHER PUBLICATIONS

Sruanganurak, Colloids and Surfaces A: Physicochem. Eng. Aspects 289 (2006) 110-117.*
Kothe, Colloids and Surfaces A: Physicochem. Eng. Aspects, 154 (1999) 75-85.*
Thongnuanchan, Polymer Engineering and Science, Apr. 2007, 47, 4, p. 421-428.*
Rabel W. Wetting, Farbe und Lacke; 77 (10), 1971, pp. 997-1006.
Owens DK, Wendt RC, J Appl Polym Sci; 13, 1969, pp. 1741-1747.
Amornchaiyapitak et al., "*Modification of Epoxidised Natural Rubber Film Surface by Polymerisation of Methyl Methacrylate*", European Polymer Journal, vol. 44, pp. 1782-1788, 2008.
Thongnuanchan et al., "Epoxidized Natural Rubber-Bonded Para Rubber Wood Particleboard", Polymer Engineering and Science, pp. 421-428, 2007.
Sruanganurak et al., "Layer-by-Layer Assembled Nanoparticles: A novel method for surface modification of natural rubber latex film", Colloids and Surfaces A: Physiochem. Eng. Aspects, vol. 289, pp. 110-117, 2006.

* cited by examiner

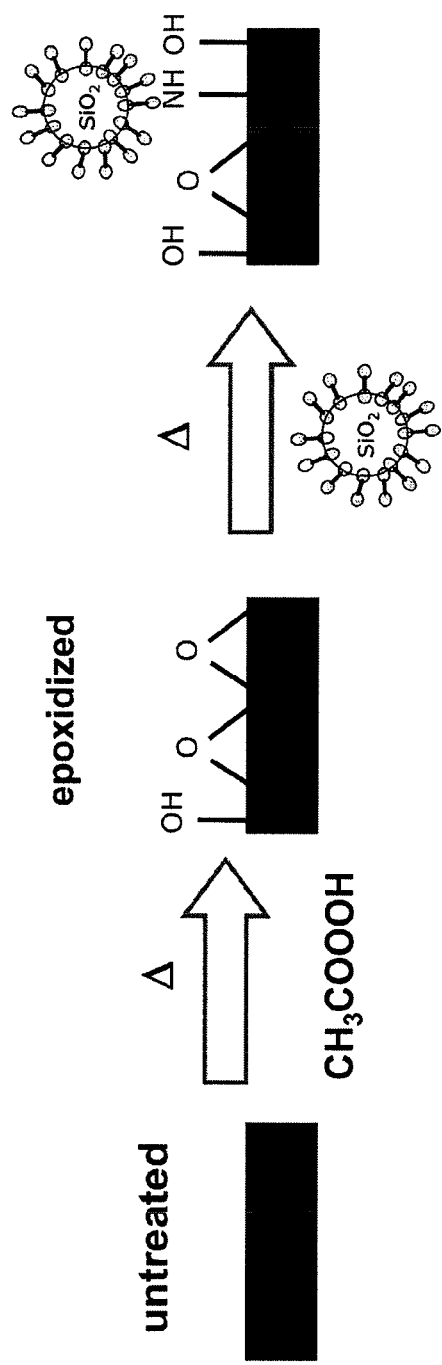

ELASTOMER PRODUCT WITH COVALENTLY BONDED PARTICLES

CROSS-REFERENCE TO RELATED APPLICATIONS

The present application claims priority under 35 U.S.C. §119(a) of Austrian Patent Application No. A 1087/2012 filed Oct. 9, 2012, the disclosure of which is expressly incorporated by reference herein in its entirety.

BACKGROUND OF THE INVENTION

1. Field of the Invention

The invention relates to a method of bonding particles to the surface of an elastomer, in particular of a glove, whereby the surface is at least partially epoxidized, as well as an elastomer product.

2. Discussion of Background Information

Modifying the surface of natural rubber gloves is already known from the prior art. For example, the surface is provided with coatings or is roughened in order to impart better lubricity to the gloves. In particular, the intention is to improve the attractability of the gloves or the attractability to moisture. Functionalization as a means of reducing potential allergies which adhere to natural rubber is also known.

One way of modifying the surface of natural rubber known from the prior art is to epoxidize the rubber surface.

For example, U.S. Pat. No. 7,442,746 A discloses a method of synthesizing an epoxidized polymer comprising the following steps: (1) producing a cationically stabilized polymer latex with at least one conjugated diolefin monomer in a first stage, (2) treating the polymer latex from step (1) with formic acid or acetic acid and hydrogen peroxide, and (3) reacting the mixture for a predefined time and at a predefined temperature in order to obtain the desired degree of epoxidation.

DE 102 60 219 B discloses a way of epoxidizing the surface layer of a rubber product whereby the rubber product is immersed in or coated with a processing fluid produced by adding hydrogen peroxide and other additives, such as surfactant, alcohol, thickening agent, a different (other) agent for reducing surface tension, to an aqueous acetic acid or formic acid solution in order to impart non-adhesive or non-stick properties, lubricity and other barrier layer properties to this surface as a result, without the occurrence of toxic gases and without causing contamination due to powder dust during the manufacturing process and without impairing (adversely affecting) the intrinsic properties of the rubber product, such as elasticity, stretch and tensile strength.

GB 1396090 A describes a method of manufacturing an object, comprising contacting an alkyl hypohalogenite or halogen-substituted alkyl hypohalogenite with an object molded from rubber with ethylenic double bonds and bonding a coating or another rubber, metal or wood to the treated surface of the molded body. Bonding may be achieved with the aid of an epoxy binding agent.

U.S. Pat. No. 5,310,819 A describes elastomer objects epoxidized at the surface, where the ethylenic bonds of the elastomer are saturated by immersing the objects in an epoxidation solution for a sufficient time.

U.S. Pat. No. 5,804,318 A discloses improved lubricating coatings for reducing the coefficient of friction of the surfaces of medical devices. The lubricious hydrogel coatings are covalently bonded to the epoxide functionalized surfaces.

U.S. Pat. No. 6,797,783 A describes a natural rubber, obtained by modifying a deproteinized natural rubber with a nitrogen content of less than 0.10% by weight, the modification comprising epoxidation of the deproteinized natural rubber with trifluoro-peracetic acid.

SUMMARY OF THE EMBODIMENTS

The objective of this invention is to propose a way of modifying the surface of elastomer gloves and of modifying elastomer surfaces.

This objective is achieved on the one hand due to the fact that, using the method outlined above, the particles are covalently bonded to the epoxide groups after the epoxidation process and in the case of the elastomer product mentioned above, the surface has particles which are at least partially covalently bonded to the elastomer.

The advantage of this is that the particles covalently bonded to the elastomer particles improve the lubricity of the elastomer products. The attractability, in particular the wet attractability, of elastomer gloves can therefore be improved. What is achieved by the covalent bond is that the improvements and changes made to the properties as a result of the surface modification lasts for a longer time. In addition, the particles impart an additional functionality to the elastomer product if the particles are chosen accordingly, for example by using particles charged with active substances. The advantage of bonding the particles by means of epoxide groups is that the elastomer surface can be epoxidized by a thermal process, in other words no actinic radiation is necessary in order to prepare the surface. Furthermore, epoxy groups that have not reacted on the surface of the elastomer reduce its tackiness and the at least partial saturation of the ethylenic groups of the elastomer improves resistance to aging.

The particles are preferably bonded by inorganic particles. This enables the tackiness to be reduced and improves attractability, in particular the wet attractability, of gloves because the contact surface of the elastomer with a hand is reduced. Generally speaking, the adhesion of an elastomer product on a surface is reduced as a result of this effect. It is also possible to impart an additional functionality to the elastomer product as a result of these solid particles, for example, if solid particles which absorb moisture are used.

in order to improve bonding of the solid particles to the functionalized surface of the elastomer product, it is of advantage if the surface of the solid particles is also functionalized before the reaction.

Accordingly, the solid particles can be functionalized by creating free mercapto groups and/or free amino groups and/or carboxylic acid groups and/or epoxide groups and/or hydroxy groups and/or anhydride groups and/or isocyanate groups and/or isothiocyanate groups on the surface of the solid particles. The advantage of using these functional groups is that they act as anchor groups with a high reactivity for bonding the solid particles to the elastomer surface.

However, the solid particles can also be functionalized by means of at least one chemical compound selected from a group comprising or consisting of acrylate groups, anhydride groups, isocyanate groups, isothiocyanate groups, methacrylate groups, vinyl groups. The advantage of using these functional groups is that anchor groups are available for bonding other functional compounds to the solid particles.

Based on another embodiment, in order to produce so-called "powder-free" elastomer products, in particular gloves, particles that are purely adhesively bonded are removed from the surface of the elastomer product. This reduces the potential allergy of the elastomer products. These particles, which have a less pronounced effect than the covalently bonded particles, can therefore optionally be recycled to the production process. This avoids contamination of wounds by particles if the elastomer product is used in the field of medicine. The elastomer product is also suitable for use in clean room environments.

Epoxidation of the elastomer may take place on a solid surface of the elastomer product. This variant of the method is used in particular for manufacturing single-layered elastomer products because this enables selected areas of the surface of the elastomer to be modified. In addition, by avoiding bulk epoxidation, the aging properties of the elastomer can be improved.

In addition to this embodiment of the method, it is also possible within the scope of the invention for epoxidation to be carried out on latex in liquid phase. This variant of the method may be used to produce multi-layered elastomer products. The advantage of this is that with this variant of the method, not only the region of the surface can be epoxidized but also the individual latex particles, thereby enabling the potential properties of the elastomer product to be adapted.

Another option is for epoxidation to take place in only discrete regions of the elastomer. This enables stronger structuring of the elastomer surface to be achieved, thereby enabling the lubricity of the elastomer to be influenced. In addition, specific properties can be imparted to specific regions of the elastomer.

The particles preferably have a particle diameter of between 10 nm and 10 μm. Although an effect was still observed with particles below 10 nm, it was nevertheless not really satisfactory in terms of improving the lubricity of the elastomer. With particle sizes of more than 10 μm, on the other hand, it was found that the improvement in bonding to the elastomer surface diminishes again due to the size of the particles.

Based on another embodiment, the particles may be at least partially cross-linked with one another. This may be achieved, for example, by means of non-reacted functional groups on the surface of the particles. This enables a "net-type" structure to be obtained. In addition, the adhesion of the particles to the elastomer surface can be improved as a result because the position of the particles can be more effectively fixed as a result of cross-linking.

The particles may incorporate at least one active substance, thereby enabling the functionalization spectrum of the elastomer surface to be significantly increased. The particles may optionally be post-loaded, resulting in a longer service life of the elastomer product.

BRIEF DESCRIPTION OF THE DRAWINGS

To provide a clearer understanding, the invention will be described in more detail below with reference to the appended drawing.

This is a schematically simplified diagram illustrating the following:

FIG. 1 Modification of NR latex films by epoxidation and subsequent bonding of amino functionalized $SiO_2$ particles.

DETAILED DESCRIPTION OF THE EMBODIMENTS

By elastomer product is meant in particular a glove, preferably a medical glove or an examination glove. However, within the scope of the invention, it is also possible to use or process or manufacture other elastomer products, for example catheters, condoms, (medical) balloons, suckers, breathing masks, etc., and immersed articles in general, in other words products which are usually produced by a dipping process.

For the sake of completeness, it should be pointed out that an elastomer product in the context of the invention is intended to mean a product made from an elastomer which has unsaturated carbon-carbon bonds in the molecular structure, i.e. in particular ethylenic bonds (=diene rubber). The elastomer is preferably a natural rubber or a synthetic isoprene rubber. In addition, the invention also lends itself to applications using other types of rubber having such unsaturated carbon-carbon bonds, in particular homopolymers and copolymers such as nitrile butadiene rubber, carboxylated nitrile butadiene rubber, polybutadiene, polychloroprene, styrene butadiene rubber.

The dipping process used to manufacture elastomer products, in particular rubber gloves, has been extensively described in the prior art. It usually involves at least the following steps: preparing a dipping mold, coagulant dipping, latex dipping. In addition, this dipping process also includes various washing and drying steps. The dipping process is usually run on a continuous basis, for example in a so-called chain dipping plant. For further details on this subject, reference may be made to the relevant prior art.

What all the embodiments of the invention have in common is that the unsaturated carbon-carbon bond is at least partially saturated by epoxidation at least in the region of the surface of the elastomer product or the elastomer (hereafter, reference will merely be made to an elastomer, this term also being intended to include the elastomer product) preferably up to at least 2%, in particular between 10% and 80%.

In principle, there are two variants of the method. Firstly, it is possible to epoxidize a solid surface of the elastomer. Secondly, another option is epoxidation in the liquid phase of the latex, after which an appropriate mold is immersed in the latex to enable the elastomer article to be produced.

In the embodiment of the method run on the solid surface of the elastomer, the elastomer product is not necessarily produced using a dipping process. It is also possible to use all other molding methods known from the prior art, for example injection molding processes, extrusion processes, compression molding, etc., although the dipping method is the preferred method of manufacturing the elastomer product within the context of the invention.

In order to saturate or bring about a reaction of the unsaturated carbon-carbon bonds on a solid surface of an elastomer product, for example an elastomer film, the elastomer surface is placed in contact with the respective reagent, for example is immersed in the epoxidation reagent or sprayed with it. The elastomer is preferably used in cross-linked form and cross-linking is preferably achieved by a photochemical process with a thiol, as described in publications AT 502 764 A1 and AT 508 099 A1. Generally speaking, in the context of the invention, cross-linking preferably takes place by a photochemical process with a thiol. However, it would also be possible to use all other types of cross-linking, for example sulfur cross-linking or peroxide cross-linking or cross-linking generally by means of actinic radiation, within the context of the invention.

Similarly, sulfur cross-linking (at increased temperature) may be used as the cross-linking method, in a manner known from the prior art.

The reagent for epoxidizing the elastomer may be, for example, an aliphatic or aromatic peracid, e.g. peracetic acid, performic acid, trifluoroperacetic acid, permaleic acid, perbenzoic acid, monoperphthalic acid, o-sulfoperbenzoic acid, p-nitroperbenzoic acid and m-chloroperbenzoic acid, the former being preferable. The concentration of peracid may be between 1% by weight and 41% by weight, in particular between 2% by weight and 4% by weight, the rest being water (with hydrogen peroxide and carboxylic acid(s)). Commercially available peracids are used.

However, it would also be possible to use other epoxidizing agents, for example hydrogen peroxide in acid or alkaline medium or tert.-butylhydroperoxide in alkaline medium, or epoxidation of the elastomer may be carried out as described in one of the above-mentioned prior arts documents, to which explicit reference may be made. It would also be possible to carry out the epoxidation using catalysts, e.g. metal-salen complex+NaOCl (Jacobsen's epoxidation) or Shi-catalyst+Oxon (Shi epoxidation).

Another option is to form peracids in situ by reacting a carboxylic acid with $H_2O_2$, e.g. in situ formation of performic acid.

The temperature at which treatment with the epoxidation reagent is carried out may be between 30° C. and 70° C., in particular between 40° C. and 50° C. Furthermore, the duration of "wetting" may be between 1 minute and 400 minutes, in particular between 40 minutes and 100 minutes. The wetted elastomer may then be immersed in water for a period of between 30 seconds and 5 minutes in order to rinse off surplus epoxidation reagent.

Finally, the wetted elastomer is dried at a temperature of between 20° C. and 100° C., in particular between 55° C. and 70° C. Drying preferably takes place within a period of between 10 minutes and 100 minutes, in particular between 15 minutes and 30 minutes.

Another option is to wet the elastomer with the epoxidation reagent in several steps, in which case intermediate drying may optionally take place between the individual steps.

As a result of epoxidation, the ethylenic double bonds react at least partially to form an oxirane ring on the surface of the elastomer, amongst other things. These oxirane rings are therefore available for the covalent bonding of the particles to the elastomer as functional groups.

Based on another variant of the method, the epoxidation is run on an optionally previously cross-linked latex in liquid phase. This latex is then formed to produce the elastomer product, for example dipped. The latex dipping may optionally be onto a previously cross-linked, preferably photochemically cross-linked, latex film, in particular, in order to manufacture an at least two-layered elastomer product.

For this method, a suspension may be produced from the latex. For stabilization purposes, at least one stabilizing agent may be added to this suspension, for example a polyethylene glycol nonyl phenylether, e.g. Synperonic® NP 30. The stabilizing agent may be dissolved in water and then added to the latex or may be added to the latex without adding more water. The total proportion of the at least one stabilizing agent may be between 2 pph and 15 pph (parts per hundred parts of rubber).

The latex may have a solid content of between 20% drc (dry rubber content) and 60% drc.

The latex may be used at a temperature of between 20° C. and 60° C.

The suspension may then be rendered acid, in which case a pH value of between 2 and 5, in particular between 3 and 4, is preferably set. In order to adjust the pH value, it is preferable to use a carboxylic acid, in particular acetic acid. However, it would also be possible to use other acids, for example inorganic acids such as HCl. In this respect, it is also possible to use a buffer. Suitable buffer substances are sodium, potassium, calcium or magnesium formiate, acetate or butyrate, sodium dihydrogen phosphate, disodium hydrogen phosphate or sodium, potassium, calcium or magnesium carbonate, sodium carbonate being preferable.

The epoxidation reagent may either be added to this suspension or created in it in situ.

For the former variant, it is preferable to use a peracid, in particular peracetic acid, although other acids may also be used, e.g. as specified above. The peracid may be used in particular as an aqueous solution with a concentration of between 1% by weight and 41% by weight.

By particular preference, a quantity of peracid is added, based on a ratio of the molar concentration of peracid to the molar concentration of polyisoprene units of the elastomer, of between 0.04 and 0.7.

If adding the peracid directly, the concentration may be between 4% mol and 70% mol, relative to the isoprene units.

If the peracid is produced in situ, the concentration of carboxylic acid may be between 10% mol and 120% mol, that of $H_2O_2$ between 10% mol and 120% mol, in each case relative to the isoprene units.

As explained above, if the epoxidation reagent is created in situ, the oxidizing agent, in particular hydrogen peroxide, and a carboxylic acid, in particular formic acid or acetic acid, are added to the suspension. The oxidizing agent and carboxylic acid may be added in equimolar quantities.

The carboxylic acid may be used in particular in the form of an aqueous solution with a concentration of between 20% by weight and 60% by weight.

The oxidizing agent may be used in particular in the form of an aqueous solution with a concentration of between 25% by weight and 50% by weight.

Particularly preferably, the oxidizing agent and carboxylic acid are added in a quantity representing a ratio of the concentration of peracid produced therefrom, in particular performic acid, to a concentration of polyisoprene units of the elastomer of between 0.1 and 0.3.

Epoxidation in liquid phase may take place at a temperature of between 20° C. (room temperature) and 80° C. and/or for a period of between 20 minutes and 60 hours.

Epoxidation of the latex particles is terminated by neutralization, for example with a 10% by weight potassium hydroxide solution.

The elastomer product is then produced from the suspension prepared in this manner, in particular by dipping a mold.

Molding may optionally be carried out in several steps, for example in two to eight repetitions.

Before and/or after epoxidation, other process chemicals may be added to the treated latex, e.g. anti-aging agents, stabilizers, antiozonants, anti-foaming agents, dyes, inorganic fillers, e.g. chalk.

In order to produce an at least two-layered elastomer product, in a first step, a first layer is produced from an elastomer, for example using a known dipping process, and this is pre-cross-linked, in particular photochemically pre-cross-linked. After at least one drying and/or optionally at least one washing step, the modified latex, functionalized as explained above, is used to apply at least one other elastomer layer to the initially produced elastomer layer, in particular by dipping. This is again followed by at least one drying and/or at least one washing step.

Particles are then applied to the surface of the elastomer, which has been epoxidized in particular by one of the two variants of the method, i.e. with epoxide groups, and these particles are covalently bonded to the elastomer surface by means of the epoxide groups, causing the rings to open.

In particular, inorganic solid particles are used, preferably solid particles of a type which are widely available. These particles are preferably selected from a group comprising or consisting of sulfides, oxides, hydroxides, carbonates, borates, sulfates, phosphates, silicates, metal particles, e.g.

gold, silver, copper. In particular, the solid particles are selected from a group comprising or consisting of chalk, diatomaceous earth, kaolinite, quartz, amorphous silicic acid, $SiO_2$, calcite, $TiO_2$.

It would also be possible to use particles with cavities, which are optionally charged with an active substance, for example zeolites or cyclodextrins. These particles may also optionally be used to adsorb substances e.g. sweat.

However, it would also be possible to use organic solid particles, for example at least partially comprising starch or cellulose, covalently bonded to the elastomer surface.

The advantage of this is that the surface of the solid particles has been functionalized prior to bonding to the epoxy groups of the elastomer surface. This functionalization may take place by creating free mercapto groups and/or free amino groups and/or anhydride groups and/or isocyanate groups and/or isothiocyanate groups and/or hydroxy groups, on the surface of the solid particles. In particular, a chemical compound may be used for this purpose, selected from a group comprising 3-mercaptopropyl trimethoxysilane, 3-mercaptopropyl triethoxysilane, 3-aminopropyl trimethoxysilane, 3-aminopropyl triethoxysilane, 3-isocyanate propyltriethoxysilane, 3-isothiocyanate propyltrimethoxysilane, hydroxymethyl triethoxysilane. These compounds may be obtained respectively from ABCR or Sigma Aldrich or Evonik Industries.

In this connection, it should be pointed out that the functionalized solid particles are for the most part at least widely commercially available, e.g. from Hoffmann Mineral or Sigma Aldrich or Evonik Industries.

However, the solid particles may also be functionalized with at least one chemical compound, selected from a group comprising or consisting of silanes, siloxanes and carboxylic acids with functional groups, such as anhydride, epoxy, isocyanate, isothiocyanate, mercapto groups. Examples of these are (3-glycidoxypropyl)trimethoxysilane, 3-(triethoxysilyl)propylsuccinic anhydrides, mercaptopropyltrimethoxysilane. These compounds may be obtained from ABCR or Sigma Aldrich.

The mercapto group is available in particular in the form of a thiol. For this purpose, it is preferable to use thiols selected from a group comprising or consisting of trimethylolpropane tris-3-mercaptopropionate, 16-mercaptohexadecanoic acid, (11-mercaptoundecyl)tetra(ethylene glycol), N-acetyl-L-cysteine, pentaerythritol tetramercaptoacetate, trimethylolpropane trimercaptoacetate, trimethylolpropane tri-3-mercaptopropionate, pentaerythritol tetra-3-mercaptopropionate, propylene glycol-3-mercaptopropionate, ethoxylated trimethylolpropane tri-3-mercaptopropionate, polyol-3-mercaptopropionate, polyester-3-mercaptopropionate. These compounds are available from Bruno Bock Thiochemicals and/or Sigma Aldrich, for example.

In addition to these preferred chemical compounds with a mercapto group, it would also be possible within the scope of the invention to use other such compounds, for example HS—R1R2R3, where R1 is an element from the group comprising or consisting of alkyl, aryl, alkylaryl, arylalkyl, alkylarylalkyl, arylalkylaryl, silyl-groups, R2 is an element from the group comprising or consisting of acryl, amino, amino acid, anhydride, carbonyl (C=O), carboxylic acid, carboxylate, epoxy, hydroxy, isocyanate, isothiocyanate, methacryl, mercapto, sulfonic acid, vinyl-groups, R3 is an element from the group comprising or consisting of H, alkyl, aryl groups.

The amino group is used in particular in the form of primary amines. To this end, it is preferable to use amines selected from a group comprising or consisting of 3-aminopropyltrimethoxysilane, 3-aminopropyltriethoxysilane, N-2 (aminoethyl)3-aminopropyltriethoxysilane.

However, it is also possible to use non-functionalized particles within the scope of the invention, especially if these are already provided with functional groups due to the chemical structure.

For functionalization purposes, the at least one thiol and/or amine and/or anhydride and/or isocyanate and/or isothiocyanate and/or the compound with the hydroxy groups are dissolved in a solvent, in particular water, and it is also possible to use organic solvents. The concentration of the at least one thiol and/or amine and/or anhydride and/or isocyanate and/or isothiocyanate and/or the compound with the hydroxy groups and/or with the at least one chemical compound, selected from the group comprising or consisting of silanes, siloxanes and carboxylic acids with functional groups, such as anhydride, epoxy, isocyanate, isothiocyanate, mercapto groups, may be between 0.1% by weight and 50% by weight, in particular between 0.5% by weight and 15% by weight, in each case relative to the total weight with the (inorganic) particles.

The respective particles used for functionalization are then added to this solution.

The solid particles may be functionalized at a temperature of between 0° C. and 200° C. and/or for a period of between 5 minutes and 720 minutes and/or at a pH value between 3 and 6. Functionalization preferably takes place accompanied by stirring.

The reaction itself may take place in both aqueous media and in liquid organic media, for example ethanol, toluene, cyclohexane, hexane, isopropanol. One possible method sequence is schematically illustrated in FIG. 1, where amino functionalized $SiO_2$ particles are used as the particles.

The advantage of this approach is that it enables a quantitative removal of non-covalently bonded particles because the tackiness of the elastomer surface is significantly reduced in the first step by the saturation of the unsaturated carbon-carbon bonds.

The functionalized particles are suspended in water or an organic solvent. The suspension is preferably produced with a concentration of between 0.01% by weight and 10% by weight, in particular between 0.01% by weight and 1% by weight, of particles modified with amino group(s) and/or mercapto group(s) and/or carboxylic acid group(s) and/or epoxide group(s) and/or hydroxy group(s) and/or anhydride group(s) and/or isocyanate group(s) and/or isothiocyanate group(s) by means of commercially available dispersing equipment. This suspension is then placed in contact with the functionalized elastomer surface, for example by immersing the elastomer in the suspension. This may optionally be done several times. Accordingly, it would also be possible for the elastomer to be only partially immersed. If immersion takes place several times, this partial immersion may be limited to one or several immersion steps, and it is also possible to opt for only partial immersion in all the immersion steps.

Treated in this manner, the elastomer may then be dried. To this end, the temperature may be selected from a range of 40° C. to 150° C., in particular from a range of 40° C. to 100° C. Drying may take place for a period of between 5 minutes and 1000 minutes, in particular for a period of between 10 minutes and 900 minutes.

The solid particles are covalently bonded to the elastomer surface during the drying process.

After bonding, it is preferable to remove particles that are purely adhesively bonded from the surface of the elastomer product, for example by washing and/or mechanically, for example by means of ultrasound.

The solid particles used for the purpose of the invention preferably have a particle size of between 10 nm and 10 µm, in particular between 20 nm and 50 nm or between 1 µm and 5 µm.

In principle, one option is to use at least one type of particles for the entire surface of the epoxidized elastomer—it would also be possible to use at least two different types of particles, for example both quartz and zeolite, in order to obtain a different property profile of the elastomer.

To this end, based on one embodiment however, the particles may be disposed only in discrete regions on the elastomer surface. In order to achieve this, the region of the elastomer surface which does not have to be further functionalized is covered by means of an appropriate mask so that during a subsequent washing step, the non-covalently bonded particles are washed away.

In this respect, in another embodiment, it is also possible to apply the particles to only discrete regions.

The mask may be a mechanical mask or a chemical mask or an optical mask. By chemical mask is meant a substance which is applied to the regions which do not have to be coated, for example painted on, before applying the respective suspensions or emulsions.

Similarly, it is also possible for the elastomer to be epoxidized only in the regions provided with the particles, in which case appropriate masks may be used for this purpose, as explained above.

In addition to imparting the pure surface structuring, it is also possible, for example, to apply permanent information to the elastomer product, for example the glove size in the case of elastomer gloves.

Based on another embodiment, the particles may be at least partially cross-linked with one another after the covalent bonding to the elastomer surface.

This cross-linking may be achieved by means of non-reacted functional groups of the functionalized particles described above, in which case an additional reagent may optionally be used, which reacts with these functional groups and thus produces a bond between the particles.

However, it is also possible to use multi-functional thiols and/or amines and/or anhydrides and/or isocyanates and/or isothiocyanates, i.e. chemical compounds with more than one mercapto and/or amino or carboxylic acid group and/or epoxide group and/or hydroxy group and/or anhydride group and/or isocyanate group and/or isothiocyanate group, such as for example trimethylolpropane-tris-3-mercaptopropionate, thereby enabling free mercapto groups to be created at least on the surface of the previously epoxidized elastomer, which will enable another reactions with other chemical compounds in order to further change the properties of the elastomer product.

In addition to the embodiment in which chemical compounds with multiple homofunctionality are used, in other words compounds having exclusively mercapto groups as functional groups in the molecule, another possibility is to use multi-functional chemical compounds with heterofunctionality. In the case of these compounds for example, in addition to at least one mercapto group by means of which the compound is bonded to the particle surface, at least one other functionality is provided, for example an amino group, a carboxylic acid group, an epoxide group, a hydroxy group, an anhydride group, an isocyanate group, an isothiocyanate group, a vinyl group, and mixed variants are also possible, in which case more than one of these groups is present in addition to the mercapto group or groups, for example a carboxylic acid group and an amino group.

If using multi-functional thiols or multi-functional amines or multi-functional polycarboxylic acids, polyalcohols, polyacetals, therefore, reactive groups may also be created on the surface of the particles, for example other thiol groups or amino groups or carboxylic acid groups.

It is also possible to use polymers with functional groups (alkenes, acrylates, anhydrides, epoxides, isocyanates, isothiocyanates, methacrylates, thiols) to modify the particles in order to obtain a covalent bond to the elastomer surface. The polymers may be used in dispersion, in solution and as a pure substance.

The functional groups may be present as side groups or independently.

The reactive groups may be used to provide the functionalized particles with other chemical compounds which are capable of reacting with these groups.

The other chemical compound may be selected from a group comprising acrylates, amines, amino acids (cysteine), acetylated amino acids (N-acetyl cysteine), anhydrides, carboxylic acids, ether, epoxides, isocyanates, isothiocyanates, methacrylates, silanes, siloxanes. This therefore results in an additional improvement to the lubricity properties and enables another functionality to be imparted (for subsequent reactions).

Depending on the reaction partner, this reaction may take place at a temperature of between 20° C. and 80° C. and on the basis of known reaction mechanisms. How long this reaction will take also depends on the respective specific compounds and may be between 1 minute and 100 minutes. The reaction may optionally be conducted under pressure or under vacuum.

Based on another embodiment of the invention, the functional groups on the particle surface which are not needed for the covalent bond to the elastomer are covalently bonded in at least certain regions to a polymer layer.

For example, the polymer layer may be made from a polyurethane or a silicone or a mixture of SBR with silicone or an acrylate or a siloxane or a polymer with functional groups, in particular alkenes, acrylates, anhydrides, epoxides, isocyanates, isothiocyanates, methacrylates, thiols, alcohols, carboxylic acids. The polymers or monomers used to form the polymer layer may likewise be functionalized beforehand, in particular with at least one type of the above mentioned functional groups.

Preferred polymers are silicones, polyurethanes, urethane acrylates, acrylates, polyisocyanates, polyesters, polyols, vinyl polymers, diene elastomers. Examples of these are Desmophen® 1652, Synthomer VL 11005, Desmolux® XP 2740, Bayhydrol® UV XP 264, Desmolux® VP LS 2299, polyvinyl alcohol, polyacrylic acid, which may be obtained from Bayer or Synthomer.

Again, suspensions are produced from the optionally functionalized polymers or monomers or oligomers (for functionalization purposes, the respective reagent may be added to this suspension), and at least one emulsifier and/or at least one photoinitiator may be added if the monomers or oligomers are to be photochemically cross-linked.

The particles may also be used to apply and/or incorporate at least one active substance. Possible active substances are, e.g. antiperspirants, antibacterial active substances, fungicides, aroma compounds, skincare products such as a vitamin or aloe vera, pigments, active substances for modifying water absorption behavior, stabilizers, etc.

The method proposed by the invention is used to functionalize the functionalization, i.e. the functionalized elastomer surface. The functional groups disposed on the surface as a result of the first functionalization therefore act as anchor groups for the other functionalization.

Using the method proposed by the invention, elastomer products can be manufactured which have a better lubricity and a better resistance to aging than is the case with an untreated elastomer. Furthermore, it is also possible to influence properties such as a skincare effect, water absorption behavior, etc., and totally new properties can be imparted to the elastomer product, such as structured elastomer surfaces, smell, color, "look and feel".

The coefficient of friction of NR surfaces modified by particles was determined using tribological measuring methods with a linear tribometer as specified by B. Bhushan, Morn tribology handbook. CLC-Press, Boca Raton, London, New York, Washington D.C. 2001, and compared with the properties of commercially sold medical gloves. The results set out in the table below demonstrate that the coefficients of friction of elastomer surfaces modified by particles fall within the range of powdered NR surfaces.

Comparison of the coefficient of friction of selected NR surfaces

| Description of sample | Coefficient of friction m |
|---|---|
| Prior art glove with chlorinated interior | m ~0.31 |
| Prior art glove with coated interior | m ~0.22 |
| Prior art glove with powdered interior | m ~0.50 |
| NR surface modified with functionalized $SiO_2$ particles | m ~0.7 |

A description will be given below of a few examples developed during the course of work on the invention, although these should not be construed as being restrictive.

The chemicals used for these examples are set out in Table 1.

TABLE 1 materials and chemicals used

| Chemical | Manufacturer | Structure formula, Specification |
|---|---|---|
| Aktisil AM | Hoffmann Mineral | Amino modified SiO2 particles (d50 = 2.2 µm) |
| Aktisil MM | Hoffmann Mineral | Mercapto modified SiO2 particles (d50 = 2.2 µm) |
| Nanoparticles | Sigma Aldrich | Amino modified SiO2 particles (d50 = 20 nm) |
| peracetic acid conc. (39 %) | Sigma Aldrich | |
| formic acid | Sigma Aldrich | |
| H2O2 | Sigma Aldrich | |
| Synperonic NP 30 | Sigma Aldrich | $C_9H_{19}$—C_6H_4—O—(CH_2CH_2O)_n—OH |

1. Modification of the Dried Film Surface
1.1 Epoxidation with Peracids

During epoxidation of the NR films, the following steps were run:
The dried latex film was washed in deionized water (10 min at RT (=room temperature, =20° C.))
The washed latex film was epoxidized in an aqueous peracetic acid solution (2% by weight) at 40° C. for 40 min
The epoxidized latex film was briefly immersed in deionized water (1 min at RT)
Drying at 70° C. for 15 min.

1.2 Epoxidation of the Liquid Phase
1.2.1 Epoxidation with Peracids

During epoxidation of the liquid NR latex, the following steps were run:
The NR latex was stabilized with Synperonic NP 30 (10 pph) and the solid content adjusted to 20-60% by weight
The latex was then acidified with acetic acid to a pH value of 3-4
Optionally peracetic acid (39% solution) was added, molar concentration ratio:

$$\frac{[Peracid]}{[Polyisopreneunit]} = 0.07 - 0.5$$

and 0.07% mol to 0.5% mol peracetic acid relative to the isoprene units
or in-situ formation of performic acid by $H_2O_2$ and formic acid with a molar concentration ratio of:

$$\frac{[H_2O_2]}{[Polyisopreneunit]} = \frac{[HCOOH]}{[Polyisopreneunit]} = 0.2 - 1.0$$

reaction temperature 21-60° C.
reaction time up to 3-48 h
reaction terminated by neutralization with a KOH solution (10% by weight)
For example, 4 g Synperonic are dissolved in 33.2 g H2O at 40° C. and added to 67 g NR (60% drc). This mixture was stirred for 15 hours. The pH was then adjusted to ~4 and 28.44 g HCOOH (98-100%) and 33.26 g $H_2O_2$ (30-%) were slowly added.

2. Producing Films of Epoxidized NR Latex

The corresponding latex films are produced in a two layer dipping process:
A pre-cross-linked NR latex is applied to a porcelain mold (20 s at RT)
Drying for 0-15 s at 120° C.
Immersion of the epoxidized NR latex (30 s at RT)
Drying for 20 min at 120° C.
Film is pulled off 3. Bonding of Inorganic Particles

EXAMPLE 1

Method Based on Aqueous Systems

During the process of bonding inorganic $SiO_2$ macro-particles, the following process steps were run:
An aqueous suspension was prepared with 0.015-0.5% by weight of commercially available amino-or mercapto-modified $SiO_2$ macro-particles by weighing the particles into deionized $H_2O$
The suspension was dispersed with a dispersing device (Ultraturax) for 10 min at room temperature and then in the ultrasound bath for 10 min at room temperature
An epoxidized NR latex film was fixed in a Petri dish
Aqueous suspension was poured over the elastomer film
Film was removed from the Petri dish after 2 min
Sample was dried for 10-900 min at 40-100° C.
Film was washed in water for 16 h at room temperature
Film was dried for 10-15 min at 70° C.

EXAMPLE 2

Method Based on Organic Solvents

A suspension was prepared with 0.015-0.2% by weight amino- or mercapto-modified $SiO_2$ macro-particles in toluene The suspension was dispersed in the ultrasound bath for 10 min at room temperature The suspension was poured over the elastomer film, tweezers being used to prevent the film from floating Film was removed from the Petri dish 2 min Sample was dried for 10-900 min at 40-100° C.

Film was washed in toluene for 16 h at room temperature

Film was dried for 10-15 min at 70° C.

EXAMPLE 3

Bonding of Nanoscale Particles

A suspension was prepared with 0.015-0.05% by weight amino-modified $SiO_2$ nanoparticles (suspended in ethanol) in toluene The suspension was dispersed in the ultrasound bath for 30 min at room temperature The suspension was poured over the elastomer film, tweezers being used to prevent the film from floating Film was removed from the Petri dish after 2 min Sample was dried for 10-900 min at 40-100° C.

Film was washed in toluene for 16 h at room temperature

Film was dried for 10-15 min at 70° C.

In technical terms, the method may be implemented directly on a chain dipping plant by dipping the gloves on the mold into the particle dispersion. To this end, it is of advantage if the particles are dispersed in the corresponding immersion tank, at least some of the time, preferably constantly, and the consumed particles are topped up. Thermal bonding may take place during the drying process or optionally during vulcanization (in the case of S-vulcanized gloves) of the gloves in the oven. The elastomer products may then be washed with water in order to remove non-bonded particles.

Alternatively, the particles may also be applied as part of the process of dipping the gloves (on the mold) in a particle slurry.

The invention claimed is:

1. A method of bonding particles to the surface of an elastomer comprising: forming an at least partially epoxidized elastomer surface by epoxidizing the surface of an elastomer and applying particles to the at least partially epoxidized elastomer surface, wherein the particles are covalently bond to the at least partially epoxidized elastomer surface.

2. The method according to claim 1, wherein the particles are inorganic particles.

3. The method according to claim 1, wherein the surface of the particles is functionalized prior to applying the particles to the surface of the at least partially epoxidized elastomer surface.

4. The method according to claim 3, wherein the particles are functionalized by creating free mercapto groups and/or free amino groups and/or carboxylic acid groups and/or epoxide groups and/or hydroxy groups and/or anhydride groups and/or isocyanate groups and/or isothiocyanate groups on the surface of the particles.

5. The method according to claim 3, wherein the particles are functionalized by at least one chemical compound selected from the group consisting of 3-aminopropyltrimethoxysilane, 3-mercaptopropyltriethoxysilane, hydroxymethyltriethoxysilane, 3-isocyanate propyltrimethoxysilane, 3-glycidoxypropyltrimethoxysilane, and 3-(triethoxysilyl)propylsuccinic anhydride.

6. The method according to claim 1, wherein particles that are purely adhesively bonded particles to the surface of the elastomer are removed.

7. The method according to claim 1, wherein the elastomer is in solid form when forming the at least partially epoxidized elastomer surface.

8. The method according to claim 1, wherein the elastomer is in liquid phase when forming the at least partially epoxidized elastomer surface.

9. The method according to claim 1, wherein epoxidation is effected on discrete regions of the surface of the elastomer when forming the at least partially epoxidized elastomer surface.

10. The method of claim 1, wherein the elastomer is in the form of a glove.

* * * * *